Figure 1:
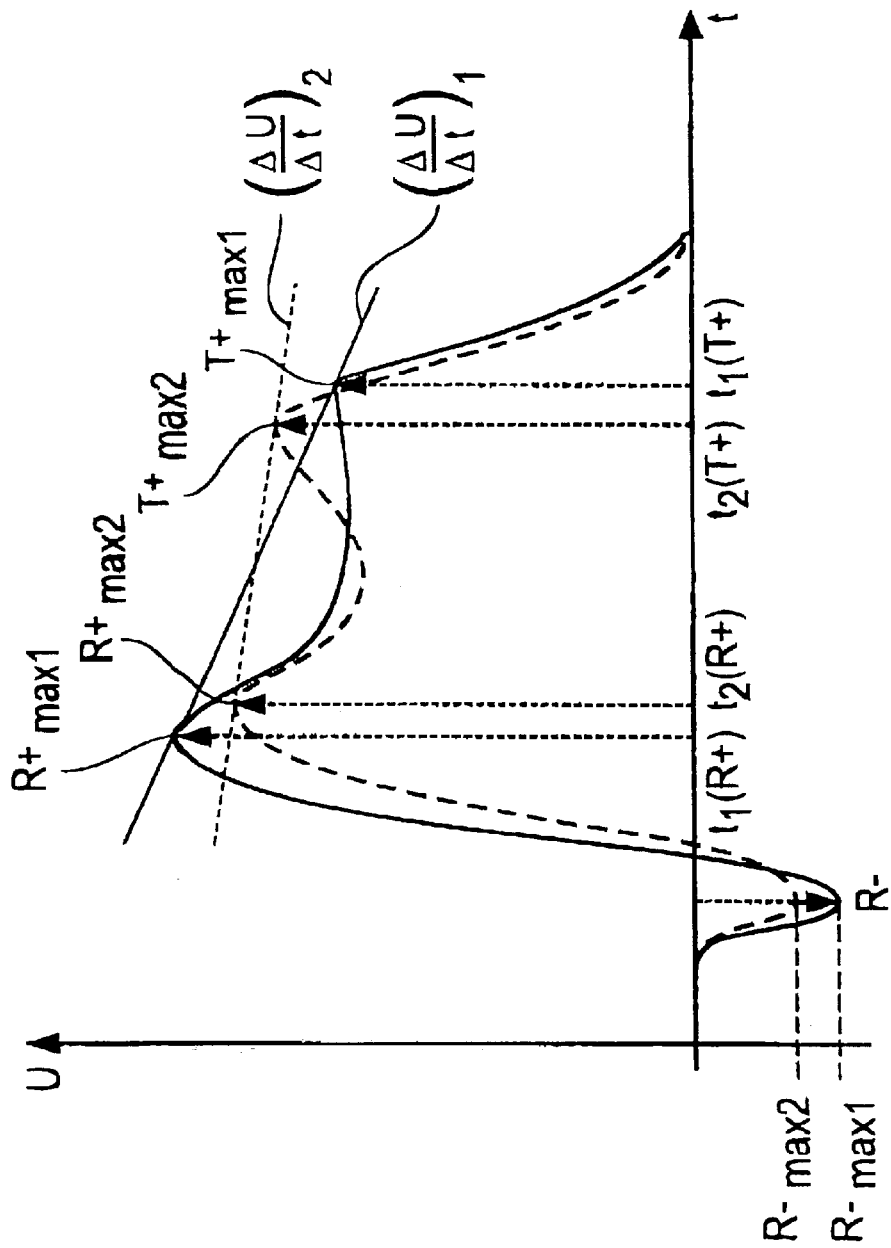

United States Patent [19]

Lang

[11] Patent Number: 6,049,734

[45] Date of Patent: Apr. 11, 2000

[54] HEART STIMULATOR WITH AV INTERVAL ADJUSTMENT

[75] Inventor: Volker Lang, Herzogenaurach, Germany

[73] Assignee: Biotronik Mess-und Therapiegerate GmbH & Co. Ingenieurburo Berlin, Germany

[21] Appl. No.: 09/213,353

[22] Filed: Dec. 17, 1998

[30] Foreign Application Priority Data

Dec. 17, 1997 [DE] Germany .................. 197 58 109

[51] Int. Cl.$^7$ .................................................. A61N 1/368
[52] U.S. Cl. ........................................................ 607/9
[58] Field of Search ......................... 607/9, 27, 28

[56] References Cited

U.S. PATENT DOCUMENTS

| | | |
|---|---|---|
| 4,108,148 | 8/1978 | Cannon, III . |
| 4,305,396 | 12/1981 | Wittkampf et al. . |
| 4,556,062 | 12/1985 | Grassi . |
| 4,781,194 | 11/1988 | Elmqvist . |
| 5,184,615 | 2/1993 | Nappholz et al. . |
| 5,534,016 | 7/1996 | Boute . |
| 5,873,895 | 2/1999 | Sholder .......................... 607/9 |

FOREIGN PATENT DOCUMENTS

| | | |
|---|---|---|
| 0232528B1 | 8/1987 | European Pat. Off. . |
| 0237767B1 | 9/1987 | European Pat. Off. . |
| 0494487A2 | 7/1992 | European Pat. Off. . |
| 0596598A2 | 5/1994 | European Pat. Off. . |
| 0601775A2 | 6/1994 | European Pat. Off. . |
| 0607951A2 | 7/1994 | European Pat. Off. . |
| 0615770A1 | 9/1994 | European Pat. Off. . |
| 0653224A2 | 5/1995 | European Pat. Off. . |
| 0716864A2 | 6/1996 | European Pat. Off. . |
| 0796636A1 | 9/1997 | European Pat. Off. . |
| 4416779A1 | 11/1995 | Germany . |
| 92/04076 | 3/1992 | WIPO . |
| 96/25976 | 8/1996 | WIPO . |

OTHER PUBLICATIONS

Der QT–Schrittmacher by Birgit Frenking & Hubertus Heuer. Pp. 255–273.

Primary Examiner—Kennedy J. Schaetzle
Attorney, Agent, or Firm—Venable; George H. Spencer; Robert Kinberg

[57] ABSTRACT

A heart stimulator, having a stimulation pulse generator and output means connected to it; a heart signal input stage for detecting evoked heart signals; an AV delay unit, connected on the output side to the stimulation pulse generator, for generating an AV interval between an atrial cardiac event or stimulation pulse, and a stimulation pulse output to the ventricle; an AV interval calculator, connected on the input side to the heart signal input stage and on the output side to the AV delay unit, for calculating the AV interval on the basis of a parameter of the heart signal; in this heart stimulator, the heart signal input stage is embodied for detecting the signal shape of evoked heart signals, and the AV interval calculator is embodied for calculating the AV interval on the basis of the heart signal shape detected.

13 Claims, 5 Drawing Sheets

HEART STIMULATOR WITH AV INTERVAL ADJUSTMENT

The invention relates to a heart stimulator as generically defined by the preamble to claim 1.

Adaptive-rate pacemakers whose stimulation frequency or rate is set as a function of signals picked up in the patient's body that reflect the physiological demand for cardiac activity on the part of the patient, have been known and used clinically in many versions for years. A review of the development goals of rate adaptation in pacemaker technology and the courses taken to pursue these goals is provided by K. Stangl et al.: *Frequenzadaptive Herzschrittmacher* [Adaptive-frequency Pacemakers], Darmstadt, 1990.

Known adaptive-rate pacemakers include the so-called QT pacemaker, in which the stimulation rate is set on the basis of the length of time between a stimulation pulse and the appearance of the T-wave in the ventricular heart actions signal initiated (evoked) by the stimulus, which is known as the QT interval (*ibid.*, pages 255–272). This time interval can be utilized to control the rate of a pacemaker, because it is dependent both on the heart rate and on exertion, and the dependency on the heart rate is virtually linear, at least within a certain time range.

According to European Patent Disclosures EP 0 232 528 B1 and EP 0 237 767 B1, the control of the stimulation rate is done on the basis of a comparison between an integrated heart action potential and a target or comparison value determined beforehand; basically, an evaluation is made of the length of time from the stimulus until the R-wave of the ventricular EKG (known as the "depolarization gradient duration").

One variable (along with the stimulation rate) that has a substantial influence on the physiological efficiency of stimulation in adaptive-rate pacemakers is the AV interval between the stimulation pulses applies to the atrium and to the ventricle. Although in early adaptive-rate pacemakers, which had a fixed rate, this interval was set to be constant and could be programmed later, this fixed setting to a constant or programmable value is hemodynamically disadvantageous in an adaptive-rate two-chamber pacemaker. Various options for automatic AV interval adaptation during pacemaker operation have therefore been proposed; see European Patent Disclosures EP 0 494 487 A2 or EP 0 596 598 A2.

From European Patent Disclosure EP 0 607 951 A2, a method for optimizing the AV interval is known, in which the AV interval is varied over a predetermined range of values at the minimum allowable stimulation rate, and the associated QT interval in each case is measured. The AV interval value for which the QT interval is maximal is then set as the optimal AV interval.

The pacemaker described in U.S. Pat. No. 5,534,016 utilizes the dependency of the T-wave in the evoked stimulus response on the set AV interval in order to fine-tune the AV interval.

The object of the invention is to furnish a heart stimulator of the generic type defined at the outset in which the AV interval is set especially dependably and is especially protected against malfunction and interference.

This object is attained by a pacemaker as defined by the characteristics of claim 1.

The invention encompasses the technical teaching of utilizing characteristic exertion-dependent changes in the signal morphology of an evoked heart signal—changes which are also not insignificantly falsified by interference or malfunction, zero-line drifting, and so forth—to control the AV interval. Components of the heart signal that are especially suitable for this purpose are the $R^-$-wave and the $R^+$-wave as well as the T-wave of the ventricular evoked response (VER).

In one embodiment, the heart signal input stage may be assigned means for detecting the maximum amplitude of the $R^-$-wave and/or the position and amplitude of the maximums of the $R^+$-wave and the $T^+$-wave of the VER, and the AV interval calculator may be embodied for calculating the AV interval on the basis of the maximum amplitude of the $R^-$-wave and/or the position and amplitude of the maximums of the $R^+$-wave and the $T^+$-wave. This embodiment is distinguished by high accuracy in the evaluation of the heart signal morphology.

In an alternative embodiment, the heart signal input stage includes means for detecting the maximum amplitude of the $R^-$-wave and/or a timer for specifying one amplitude value detection time each and means for detecting the amplitude values at the respective detection time in the region of the $R^+$-wave and the $T^+$-wave of the VER, and the AV interval calculator (100B) is embodied for calculating the AV interval on the basis of the maximum amplitude of the $R^-$-wave and/or the amplitude values in the region of the $R^+$-wave and the $T^+$-wave. This embodiment can be achieved more simply and more economically in terms of electric current, since the amplitude values of the $T^+$-wave and $T^-$-wave are evaluated at specified times after the stimulation pulse, and there is no need to search by computer for the various local maximums. The detection times in the simplest case are kept invariant when the AV interval varies, and/or are kept invariant when changes in the stimulation rate occur.

In a preferred embodiment, the AV interval calculator includes arithmetic means for determining the slope—or more precisely, the quantitative slope—between the maximums or the pairs of amplitude value detection time values for the $R^+$-wave and the $T^+$-wave, which is used selectively as a relevant variable for optimizing the AV interval. As an alternative to this, or at the same time, the quantity of the amplitude value of the $R^-$-wave can be evaluated.

Ascertaining the physiologically optimal AV interval is done in setting phases or cycles, in which with a stimulation rate kept fixed, a predetermined range of values for AV interval values is run through, and the AV interval value in which an assessment criterion for the signal morphology is best met is selected as optimal. In particular, this can be the AV interval at which the quantitative slope of the VER between the maximums or the pairs of amplitude value detection time values of the $R^+$-wave and the $T^+$-wave and/or the amplitude value of the $R^-$-wave is maximal.

The AV interval calculator or the AV delay unit itself is preferably embodied for outputting a substitute AV interval value if a current calculated AV interval result is unavailable, especially if the stimulation pulse generator (102) is inhibited or an evoked heart signal is not detected, or in the event that over a relatively long period of time the patient fails to assume a resting state suitable for the measurement. This is expedient because a prerequisite for performing a calibration cycle to calculate the physiologically optimal AV intervals is the presence of an evoked response and as much as possible a recumbent state, with little exertion on the part of the patient, and the calibration cycle is therefore impossible if pacemaker operation is inhibited and/or in a persistent state of high patient exertion.

Figure 2:
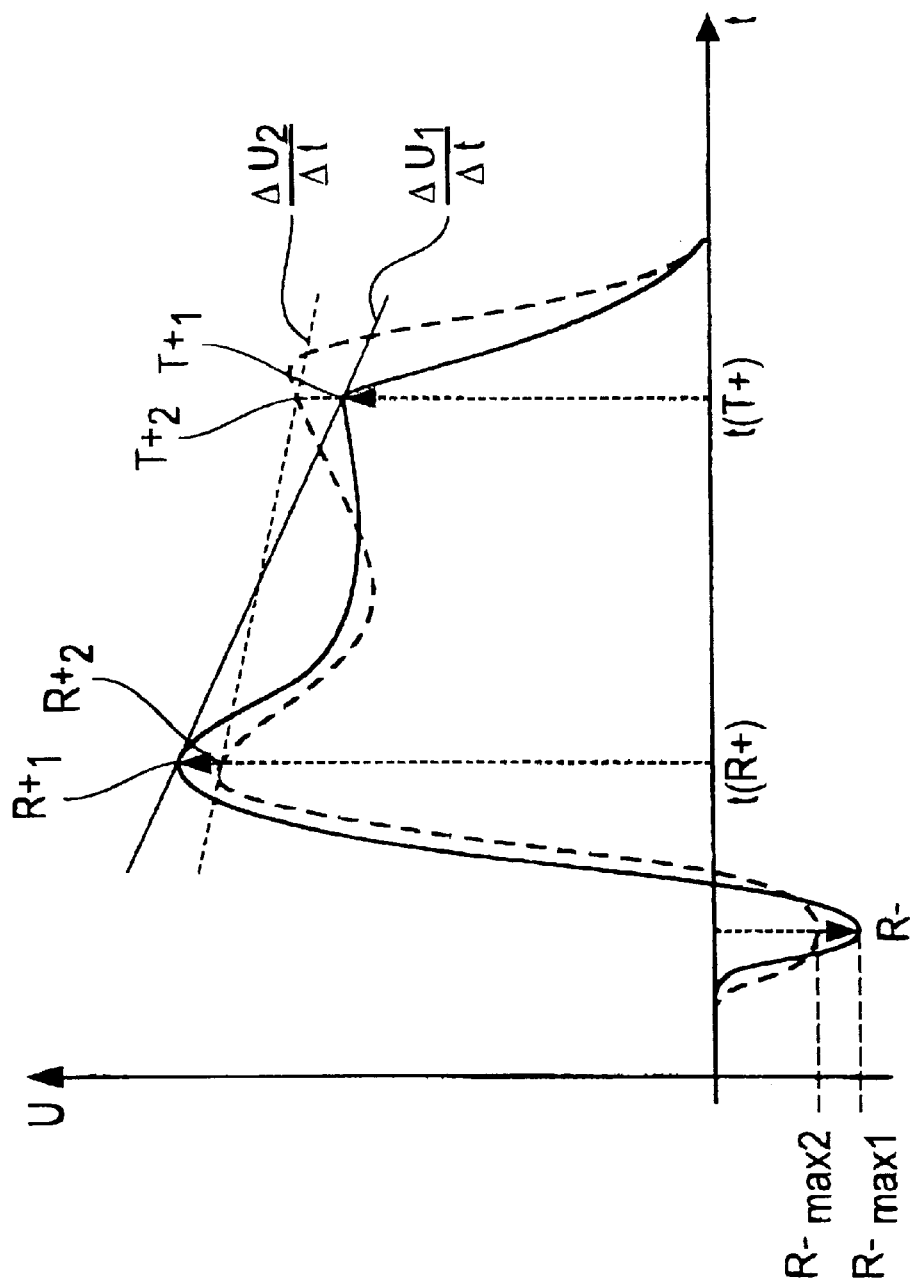
Figure 3:
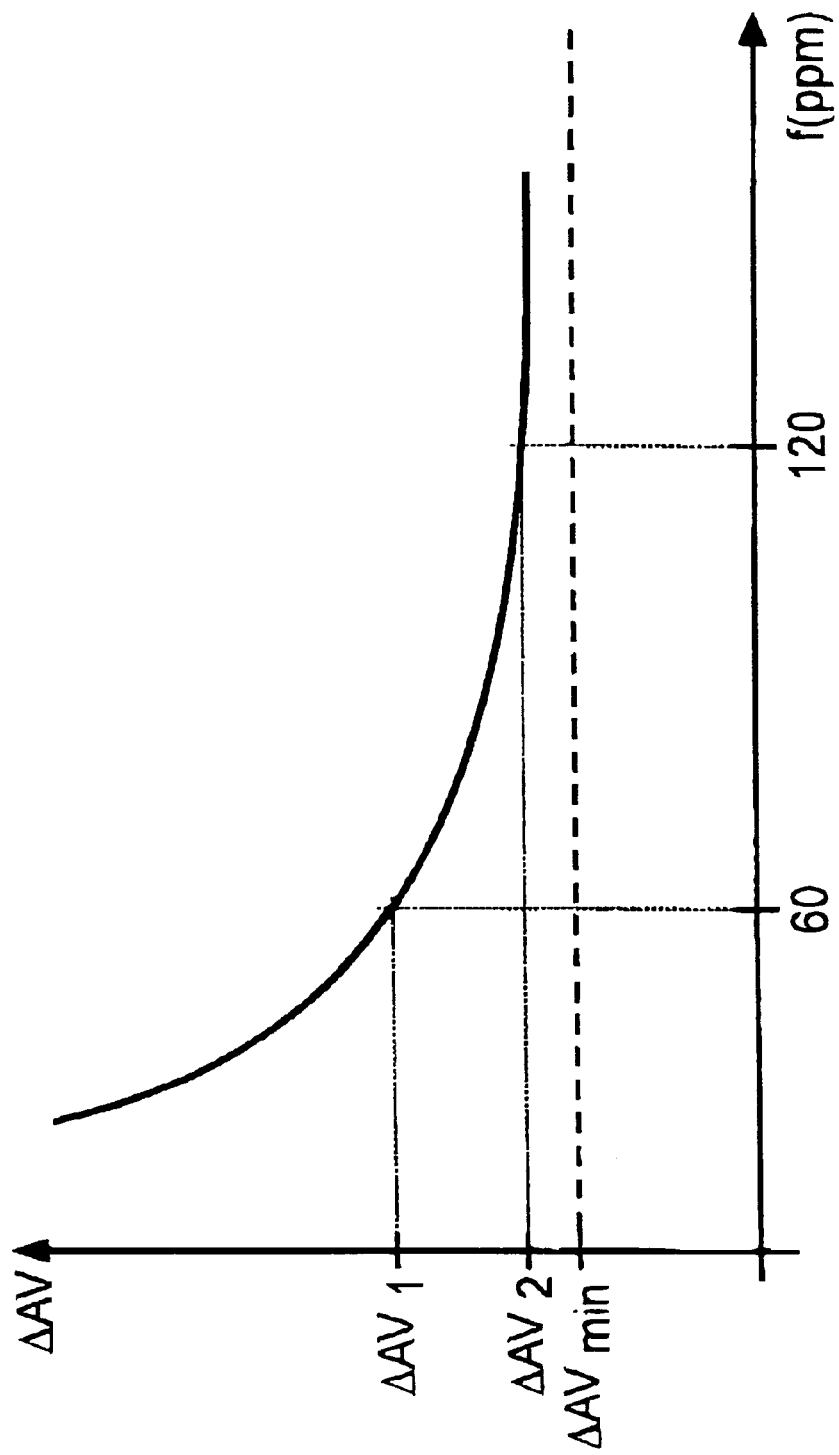
Figure 4:
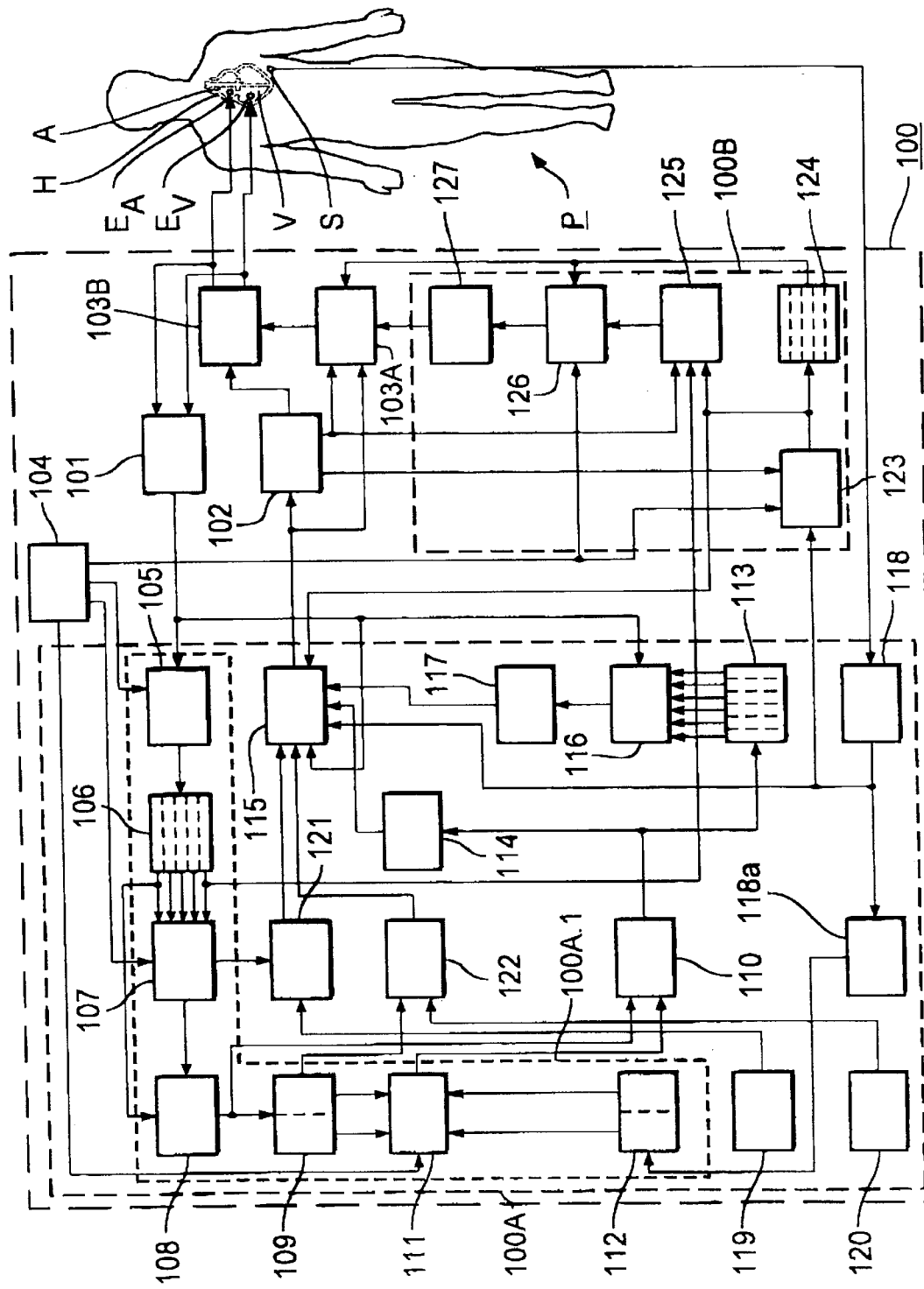
Figure 5:
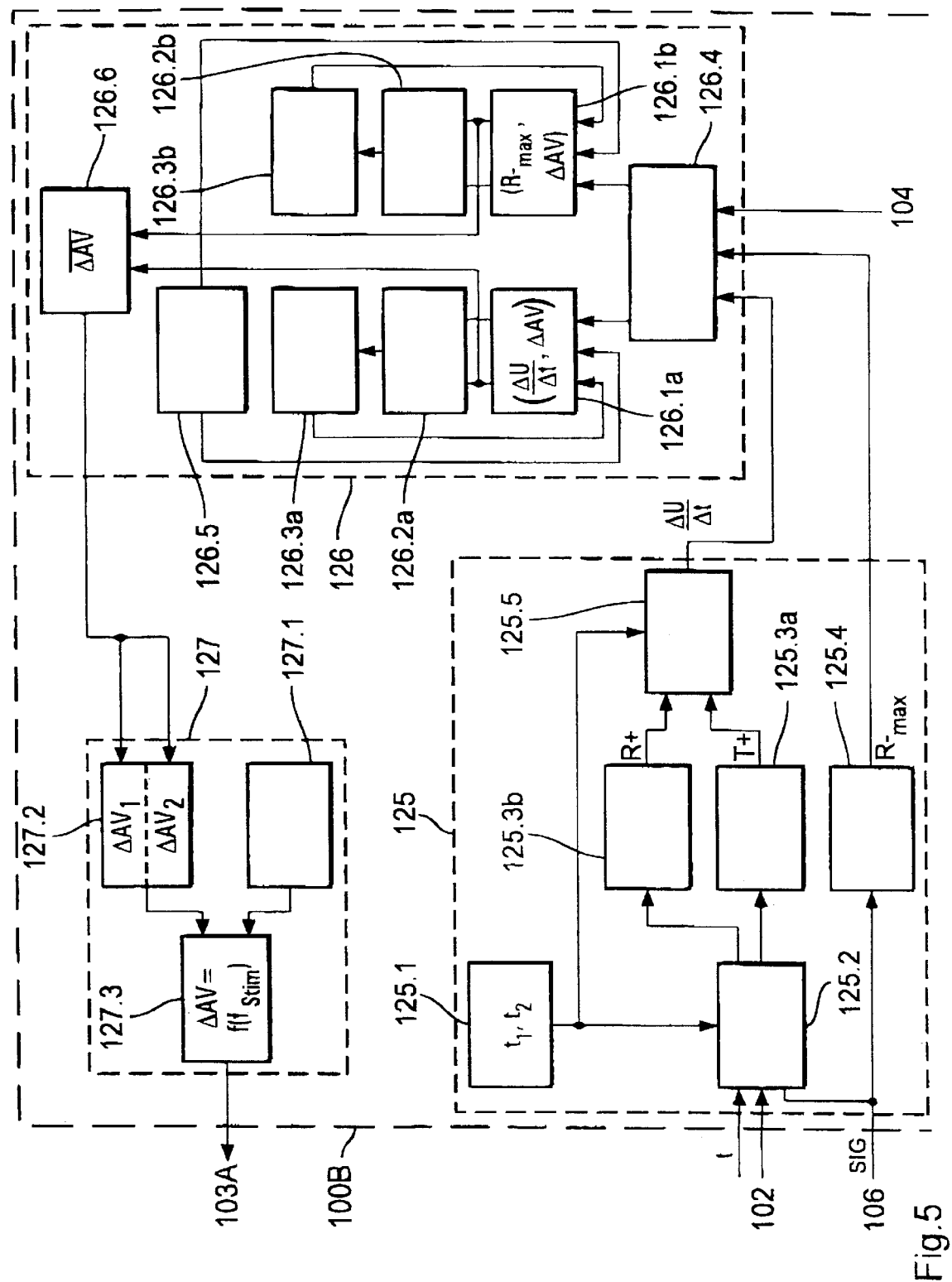

Advantageous refinements of the invention are also defined by the dependent claims and will be described in further detail below along with the description of the preferred embodiment in conjunction with the drawings. Shown are:

FIG. 1, a graph for evaluating the signal morphology of the VER for AV interval control in one embodiment of the invention;

FIG. 2, a graph for evaluating the signal morphology of the VER for AV interval control in a further embodiment of the invention;

FIG. 3, a graph showing the relationship between the AV interval and the stimulation frequency in one embodiment of the invention;

FIG. 4, a block circuit diagram showing the function of various components of an adaptive-rate two-chamber pacemaker in one embodiment; and FIG. 5, a detailed view of the pacemaker of FIG. 4.

FIG. 1 is a schematic graph showing the $R^-$-wave, the $R^+$-wave, and the $T^+$-wave of two VER signals $VER_1$ and $VER_2$ picked up at a constant stimulation frequency and with different AV interval values; the signal voltage U is plotted over time t from when the stimulation pulse is emitted. It can be seen from the curves that the maximum signal voltages $R^{-max1, R-max2 \text{ in the } R-}$ segment differ, just as do the location and voltage value of the amplitude maximums in the $R^+$ and $T^+$ segments of the VER. It is clear from this that evaluating the signal morphology for controlling the AV interval is advantageously possible on the basis of a comparison of the maximum signal amplitudes in the $R^-$ region—per se—and the relationships between the amplitudes in the $R^+$ and $T^+$ region. For mathematically evaluating this last relationship, it is especially suitable to calculate the rise $\Delta U/\Delta t$ between the local maximums $R^+_{max}$ and $T^+_{max}$ in the individual VER signal courses in the region of the $R^+$-wave and the $T^+$-wave. The straight rise curves $(\Delta U/\Delta t)_1$ and $(\Delta U/\Delta t)_2$ are also shown in the drawing.

Within a predetermined quantity of AV intervals, in accordance with a preferred optimization algorithm, the interval value at which both $R^-_{max}$ and $\Delta U/\Delta t$ becomes minimal should be considered optimal; however, other optimizing or assessment criteria are also possible.

FIG. 2 is a graph, similar to FIG. 1, showing two different VER signal courses. The above description of FIG. 2 is therefore referred to with respect to the individual variables involved. Unlike FIG. 1, here it is not the relationship between the maximum amplitudes of the $R^+$-wave and $T^+$-wave that are evaluated, though, but the relationship between the amplitudes at predetermined times $t(r+)$ and $t(t+)$. That is, the slopes $\Delta U_1/\Delta t$ and $\Delta U_2/\Delta t$ between the points $R^+_1$ and $T^+_1$ or $R^+_2$ and $T^+_2$ are determined and evaluated. This makes it considerably simpler to evaluate the signal course and is sufficient for certain optimization applications, although the chronological location of the local maximum in the region of the $T^+$-wave is not exertion-dependent.

FIG. 3 schematically shows the dependency of the AV interval $\Delta AV$ on the stimulation frequency f, the so-called Bezeet curve, which is used to set the optimal AV interval for arbitrary stimulation frequency values on the basis of two calibration valves (designated $\Delta AV_1$ and $\Delta AV_2$ in the drawing).

For calibration, at the at least two fixed stimulation frequencies (in this example, 60 and 120 ppm), one AV interval value region each is scanned, and the associated measured value quantity of signal parameters is assessed as described above in accordance with at least one previously defined criterion, in order to find the optimal AV interval for the fixed frequency. Two series of measurements, at a low frequency and a high frequency with an unchanged patent status—preferably while recumbent and at rest—are usually sufficient to find the valid Bezeet curve and thus to make an associated specific AV interval value available for every frequency value occurring in ensuing normal pacemaker operation.

Since the evoked heart signals develop only upon stimulation, and intrinsic signals cannot be used for the above-sketched determination of a signal shape parameter, a P-synchronous ventricular stimulation that is uninterrupted in terms of phase, must be assured for AV interval adaptation for the duration of the calibration process, even if the patient's own heart rate may be adequate under some circumstances. Furthermore, because of the nonphysiological influence of the differential parameter associated with fusion beats (that is, the virtually simultaneous occurrence of a stimulation pulse and spontaneous heart action), the incidence of fusion beats must be prevented. To make it possible to perform not only the more-unproblematic measurement series at high frequency (overstimulation) but also a measurement series at low stimulation frequency, the presence of a status of low intrinsic heart rate should be assured for the duration of the measurements. If this cannot be achieved well enough by selecting a resting phase, then medication can be given to support it. Up to a certain extent, raising the lower measurement frequency above the intrinsic rate can also make sufficiently precise measurements possible.

In FIG. 4, in the form of a block circuit function diagram, essential elements of an adaptive-rate pacemaker 100 are shown; for the sake of simplicity, pacemaker components that are known per se but are not essential to realizing the invention have been omitted.

The pacemaker 100 is connected on the input and output sides with two intracardial electrodes, $E_A$ in the atrium and $E_V$ in the ventricle V, of the heart H of a patient P and to a combined position and activity sensor S. Via the ventricular electrode $E_V$, ventricular heart signals detected are delivered to the input of a heart signal input stage 101 (known per se) embodied for accurate-signal-shape detection of intracardial EKG signals. Atrium signals appearing at the atrial electrode $E_A$ are also delivered to the heart signal input stage 101; however, they are used only in the usual way to fix the stimulation timing, and their morphology is not evaluated. Stimulation pulses generated by a stimulation pulse generator 102 are output to the atrium A and ventricle V via an AV interval delay unit 103A and an output stage 103B and the respective electrodes $E_A$ and $E_V$.

The pacemaker 100 includes a sequence controller 104, which controls the entire course of operation—in the drawing, however, for the sake of simplicity, only the control signal connections to some components important in this context are shown.

The generation and furnishing of the rate control signals for controlling the stimulation rate in accordance with the physiological demand of the patient P is done in a rate calculator 100A, connected on the input side both to the heart signal input stage 101 and the activity sensor S and on the output side to the stimulation pulse generator 102, which as its most essential function block has a signal amplitude processing unit 100A.1.

The signal amplitude processing unit 100A.1 includes a serial heart signal memory 106, connected to the heart signal input stage 101 via an A/D converter and memory access unit 105 (which in turn is triggered by the sequence controller 104), with a plurality of memory regions each for one complete evoked ventricular heart action (VER). A variation evaluation unit 107 and a subtraction stage 108—the former also controlled by the sequence controller 104—are connected to the output of the memory 106.

In the variation evaluation unit 107, for a predetermined period of time or a predetermined number of evoked heart signals (in accordance with a program stored in the sequence controller 104, either a single time or at predetermined relatively greater intervals), those segments or times of the VER signal for which the difference in signal amplitudes exhibits maximum variability are ascertained. In the subtraction stage 108, for whichever is the last heart signal U(t) picked up, the current differential amplitude value $\Delta U = U_2(t_2) - U_1(t_1)$ is formed continuously at these two cycle times (also known as adaptation or differential parameters). On the output side, the subtraction stage is connected to a differential amplitude memory 109 and a recalculation stage 110. In the differential amplitude memory 109, whichever are the greatest and least differential amplitude values detected—which are continuously updated—are retained in memory and delivered to an input pair of a standardizing stage 111, which via a second input pair is connected to a rate limit value memory 112, in which the minimum and maximum allowable stimulation rates for rate control are stored in memory.

In the standardizing stage 111, from the available minimal and maximal values for the amplitude difference and the minimal and maximal values for the stimulation rates, the current valid physiological course of the differential parameter is ascertained as a function of the stimulation rate and delivered to the recalculation stage 110. In that stage, from this and from the current value of the differential parameter obtained from the subtraction stage 108, the current rate control signal is calculated by the procedure described above.

The recalculation unit 110 is connected on the output side in parallel to a rate control signal memory 113 and a smoothing stage 114. The smoothing stage 114, in which (in a manner known per se) reprocessing of the rate control signal is done to avoid excessively large "rate jumps", is connected to an input of a switchover unit 115, by way of which the rate control signal, under the conditions described below, is finally switched through to the stimulation pulse generator.

The rate control signal memory 113 is connected to the input of a trend calculation stage 116, which is connected to the heart signal input stage 101 via a control signal connection and is activated by this stage if no VER signal is detected. The trend calculating stage 116, after its activation, loads the stored rate control signals in chronological order and performs a trend calculation for them, the result of which is output at a substitute control signal calculating unit 117. This unit in turn, continuing the trend calculated, calculates a substitute rate control signal. This signal is switched through by the switchover device 115—which is also activated via the heart signal input stage 101—in order to replace the original rate control signal, which was unavailable in the absence of a VER signal, for the stimulation pulse generator.

The position and activity sensor S is connected to a sensor signal processing unit 118, which—in accordance with known algorithms—calculates a further substitute rate control signal from the activity signal, and this further signal is furnished to a further input of the switchover unit 115. The sensor signal processing unit 118 also forms whichever is the valid stimulation rate maximum value and transmits it to the memory 112.

The rate calculating device 100A also includes a variation width memory 119 and a maximum differential amplitude value memory 120, in which essential peripheral conditions for the range of applications of the embodiment proposed, on the one hand a minimum allowable amplitude variability value and on the other the maximum allowable differential amplitude value or differential parameter value, are stored. The stored values are subjected, in a variability comparator unit 121 or a differential amplitude comparator unit 122, to a comparison with the respective actual values, which are delivered to the comparator units 121, 122 by the variation evaluation unit 107 or the differential amplitude memory 109. If the outcome of the comparison is that one of the required peripheral conditions is not met, then by the outputting of a suitable control signal by the comparator units 121, 122 to the switchover unit 115, the substitute rate control signal generated by the sensor signal processing unit 118 is switched through to the stimulation pulse generator, instead of the rate control signal calculated on the basis of the signal morphology.

Along with the rate calculating device 100A, the pacemaker 100 also has an AV interval calculator 100B, which is likewise activated and controlled via the sequence controller 104. The activation is effected via a two-stage AND gate 123, whose first input is connected to the output of the sequence controller 104, whose second input is connected to the output of the stimulation pulse generator, and whose third input is connected to the output of the sensor signal processing unit 118. The AND gate 123 allows a (periodically emitted) activation signal of the sequence controller 104 to pass, in order to initiate and AV interval determination, only if an output signal of the sensor signal processing unit 118 which indicates the patient P is recumbent or at rest, and a signal from the stimulation pulse generator which characterizes the outputting of stimulation pulses, are both present simultaneously. This assures that an AV setting cycle will be executed only if the patient is resting or in the recumbent state and the pacemaker is not inhibited, that is, if the heart signals detected actually represent evoked potentials.

If these conditions are met, then via the AND gate 123, for a predetermined measurement series, a first predetermined stimulation rate is fixedly set at the switchover unit 115, on the one hand, and on the other a sequence of AV interval values is transferred sequentially from an AV interval preselection memory 124 to the AV delay unit 103A. With these values, a number of two-chamber stimulations—the number is programmed in the sequence control unit 104—are executed, and in each of the stages 101 and 105 a stabilized, digitized VER signal shape is obtained and stored in the memory 106.

During or after the first measurement series at the first stimulation frequency, an evaluation, sketched out in principle above and described in further detail hereinafter, of each individual VER signal shape among those buffer-stored in the memory 106 is performed in a signal shape evaluation unit 125. In a following measurement series assessment unit 126, to which the AV interval value corresponding to each signal shape curve is supplied from the preselection memory 125, a summarizing assessment of the results of evaluation of the measurement series is carried out, on the basis of at least one assessment criterion stored internally in memory. At the output of the measurement series assessment unit 126, the optimal AV interval value corresponding to the first set stimulation frequency is then available and is delivered to a Bezeet curve evaluation unit 127.

As soon as this has been done, then via the sequence controller 104 a second, identical kind of measurement series is initiated and executed at a second, fixedly set stimulation frequency; the result of this is that an optimal AV interval corresponding to the second stimulation frequency is ascertained and transferred to the Bezeet curve evaluation unit 127. Once it is received there, a selection procedure from among a family of function curves stored in advance is performed on the basis of the two values $\Delta AV1(f1)$ and $\Delta AV2(f2)$ that are present, and as a result, the currently valid function curve $\Delta AV=f(f)$ is available.

This curve is transferred to the AV delay unit 103A and stored in memory there. The AV delay unit is connected directly, along with the stimulation pulse generator 102, to the output of the stimulation frequency switchover unit 115, and because of the Bezeet curve stored in memory, as pacemaker operation continues, it assigns a specific AV interval to each current value, forwarded from the pacemaker, for the stimulation frequency, so that the next chamber stimulus to be output will be delayed relative to the associated atrial stimulus.

In the event that calibration cycles cannot be executed in turn because of persistent inhibition of the pacemaker, or for other reasons, then the AV delay unit 103A uses one or more programmed substitute AV intervals, each fixedly assigned to one stimulation frequency. Alternatively, the AV interval calculator 100B can—analogously to what has been described above for the rate calculating unit 100A—include means for extrapolating past values, which make it possible to extrapolate from an observed trend.

FIG. 5—again in the form of a block circuit function diagram—shows the layout and function of the most important components of the AV interval calculator 100B of FIG. 4 in more detail.

The signal shape evaluation unit 125, in the version shown in FIGS. 4 and 5, has connections on its input side both to the stimulation pulse generator 102 and to the heart signal memory 106, and also naturally (which is not shown in FIG. 4, and is symbolized by the input signal "t" in FIG. 5) to a central timer for the pacemaker. Thus along with the actual signal shape information SIG, it receives timing information about both the stimulation pulse and the heart signal evoked by the stimulation pulse. Combining the various individual items of timing information for heart signal courses related to the applicable stimulation pulse and at the same time assigning two scannng times t(R+), t(T+) (see FIG. 2) are done in a scanning time correlation stage 125.2. Its output is connected to two amplitude detectors 125.3a and 125.3b. They detect the amplitude values of the heart signal at the times t(R+) and t(T+), while a parallel-connected multistage amplitude discriminator 125.4 detects the maximum amplitude in the range of negative signal polarity, i.e. the amplitude $R^-_{max}$ for the applicable $R^-$-wave.

The amplitude detectors 125.3a, 125.3b are connected on the output side to an arithmetic calculating unit 125.5, which also receives the scanning times from the working memory 125.1 and calculates the slope $\Delta U/\Delta t$ of the heart signal in the range of the $R^+$-wave relative to the $T^+$-wave (FIG. 2) from the scanned amplitude values and scanning times. Thus as the outcome of the evaluation of each individual heart signal, the signal shape parameters $R^-_{max}$ and $\Delta U/\Delta t$ are available at the output of the signal shape evaluation unit 125.

The measurement series calculating unit 126 includes one dual-region parameter memory 126.1a, 126.1b each for storing the signal shape parameter pairs of both an earlier heart signal curve and the most recently analyzed heart signal curve, together with the corresponding AV interval value, and a respective comparator unit 126.2a, 126.2b associated with each of the parameter memories 126.1a, 126.1b. The inputs of the comparator units are each connected to the two memory regions in which the parameter values of the present heart signal and of the earlier heart signal are stored, and these values are compared with one another. By means of a control signal output as the result of the comparison, one memory erasing controller 126.3a or 126.3b, respectively, is activated, which erases the contents of whichever memory region has the larger value, $R^-_{max}$ or $\Delta U/\Delta t$. As the outcome of the sequential morphology comparisons, whatever is the least value, so far, of the signal shape parameter (together with the associated AV interval value) thus remains stored in memory step by step, and is used for comparison with the currently analyzed heart signal. To that end, its parameter values are written, by means of a memory writing controller 126.4 connected on its input side to the sequence control unit 104, into the memory regions of the memories 126.1a, 126.1b that have been freed up by the erasure.

Once each measurement series in concluded, at a fixed stimulation frequency, the minimal values $(R^-_{max})_{min}$ or $(\Delta U/\Delta t)_{min}$ and the respective associated AV interval values remain in the memories 126.1a, 126.1b. The two AV interval values are transferred by a memory access controller 126.5 to an averaging stage 126.6, where the AV interval value averaged from the evaluation of both signal shape parameters, is calculated. In the averaging stage 126.6, an arithmetic average can be formed from the AV interval value pertaining to $(R^-_{max})_{min}$ and $(\Delta U/\Delta t)_{min}$. The algorithm stored in memory may, however, also include a higher weighting or prioritizing of one of the signal shape parameters, to determine which AV interval is to be considered optimal overall.

The Bezeet curve selection unit 127 includes a function curve memory 127.1, in which a family of function curves $\Delta AV=f(f_{Stim})$ has been stored in advance, and a dual-region AV memory 127.2, which is connected to the averaging stage 126.6 and into whose two memory regions, in the course of a calibration procedure, the AV interval values ascertained as being optimal for two stimulation frequencies are written. The nucleus of the selection unit 127 is an adaptation stage 127.3 of conventional design, in which after the second AV interval value for the calibration is received from the averaging stage 126.6, the valid Bezeet curve (FIG. 3) is automatically ascertained on the basis of the AV interval values stored in the memory 127.2.

The invention is not limited in its realization to the preferred exemplary embodiments described above. On the contrary, a number of variants is conceivable that make use of the version shown and described here, even in different kinds of embodiments.

For instance, in addition to the embodiment in the form of the pacemaker with automatic adaptation of the AV interval as described above, an embodiment by means of a pacemaker programmer/PC configuration in the context of followup studies is also possible. An optimized AV interval for a conventionally programmable pacemaker can be ascertained by means of an AV interval calculation algorithm implemented in the external computer and then programmed in the pacemaker in the usual way by means of the programming device. If the application in particular involves a pacemaker in which an association between various AV interval and stimulation rate values is provided, then in this way—following the principle sketched out above—the stored association table can be updated.

Besides in an adaptive-rate two-chamber pacemaker, the invention can in principle be realized in other heart stimulators as well, in which it is important to adhere to an optimized time interval between an atrial event and a ventricular stimulus, such as in atrium-synchronized single-chamber pacemakers and in certain defibrillator or cardioverters.

I claim:

1. A heart stimulator arrangement (100), having
    a stimulation pulse generator (102) and output means (103B, $E_V$) connected to it for outputting stimulation pulses to the ventricle (V) of a heart (H),
    a heart signal input stage (101) for detecting evoked heart signals, in particular the ventricular evoked response VER,
    an AV delay unit (103A), connected on the output side to the stimulation pulse generator, for generating an AV interval ($\Delta AV$) between an atrial cardiac event or atrial stimulation pulse and a stimulation pulse output to the ventricle,
    an AV interval calculator (100B), connected on the input side to the heart signal input stage and on the output side to the AV delay unit, for calculating the AV interval on the basis of at least one parameter of the heart signal,
    characterized in that
    the heart signal input stage is embodied for detecting the signal shape of evoked heart signals, in particular the morphology of the ventricular evoked response (VER), and the AV interval calculator is embodied for calculating the AV interval on the basis of the heart signal shape detected.

2. The heart stimulator arrangement of claim 1, characterized in that means (125.4) for detecting the maximum amplitude ($R^-_{max}$) of the $R^-$-wave and/or the position and amplitude of the maximums of the $R^+$-wave and the $T^+$-wave of the VER are provided, and the AV interval calculator (100B) is embodied for calculating the AV interval on the basis of the maximum amplitude of the $R^-$-wave and/or the position and amplitude of the maximums of the $R^+$-wave and the $T^+$-wave.

3. The heart stimulator arrangement of claim 1, characterized in that means (125.4) for detecting the maximum amplitude ($R^-_{max}$) of the $R^-$-wave and/or a timer (t) for specifying one amplitude value detection time each ($t_1$, $t_2$) and means (125.3a, 125.2b) for detecting the amplitude values ($R^+$, $T^+$) at the respective detection time in the region of the $R^+$-wave and the $T^+$-wave of the VER are provided, and the AV interval calculator (100B) is embodied for calculating the AV interval on the basis of the maximum amplitude of the $R^-$-wave and/or the amplitude values in the region of the $R^+$-wave and the $T^+$-wave.

4. The heart stimulator arrangement of claim 3, characterized in that the detection times ($t_1$, $t_2$) are kept invariant when the AV interval varies, and/or are kept invariant when changes in the stimulation rate occur.

5. The heart stimulator arrangement of claim 2, characterized in that the AV interval calculator (100B) has arithmetic means (125.5) for determining the slope ($\Delta U/\Delta t$) between the maximums or the pairs of amplitude value detection time values for the $R^+$-wave and the $T^+$-wave.

6. The heart stimulator arrangement of claim 1, characterized by
    an AV interval preselection memory (124) for storing a predetermined quantity of AV interval values,
    a sequence control unit (105, 123) for sequence control of an AV interval setting cycle with successive, temporary setting of a plurality of stored AV interval values,
    a heart signal memory (106; 125.2) for storing a plurality of heart signal courses detected during the AV setting cycle each in association with the set AV interval value,
    a signal shape evaluation unit (125, 126), connected to the heart signal memory, which from each stored heart signal course ascertains at least one signal shape parameter value and subjects the signal shape parameter values ascertained to evaluation on the basis of a programmed assessment criterion, and
    an AV interval selector unit (127) for setting the AV interval value or the particular functional dependency between AV interval values and stimulation frequency values that is associated with the heart signal course that is assessed as optimal by the signal shape evaluation unit.

7. The heart stimulator arrangement of claim 6, characterized in that the programmed assessment criterion is the amplitude value of the $R^{-wave\ and/or\ the\ quantitative\ slope\ of\ the\ VER\ between\ the\ maximums\ of\ the\ R^+}$-wave and the $T^+$-wave.

8. The heart stimulator arrangement of claim 1, characterized in that the AV interval calculator (100B) or the AV delay unit (103A) is embodied for outputting a substitute AV interval value in the absence of a current calculated AV interval result, in particular if the stimulation pulse generator (102) is inhibited or an evoked heart signal is not detected.

9. The heart stimulator arrangement of claim 1, characterized by a position and/or activity sensor (S) and by a sequence controller (105, 123), connected to it via a control input, for controlling an AV interval calibration procedure as a function of the output signal of the position and/or activity sensor.

10. The heart stimulator arrangement of claim 1, characterized by the embodiment as an adaptive-rate pacemaker (100) with means (100A) for exertion-dependent setting of the stimulation frequency and means (127) for associating a specific AV interval value with at least some of the stimulation frequency values.

11. The heart stimulator arrangement of claim 1, characterized by the embodiment as a two-chamber pacemaker (100) with means (103B, $E_A$) for outputting stimulation pulses to the atrium (A).

12. The heart stimulator arrangement of claim 1, characterized in that the AV interval calculator is provided externally to an implantable heart stimulator, in particular in a programming device or in an accessory to it.

13. The heart stimulator arrangement of claim 1, characterized in that the AV interval calculator (100B) is embodied as a component of an implantable heart stimulator (100).

* * * * *